(12) United States Patent
Arai et al.

(10) Patent No.: US 10,534,048 B2
(45) Date of Patent: Jan. 14, 2020

(54) MAGNETIC RESONANCE IMAGING APPARATUS AND SAR PREDICTION METHOD

(71) Applicant: HITACHI, LTD., Tokyo (JP)

(72) Inventors: Koichi Arai, Tokyo (JP); Takeshi Yatsuo, Tokyo (JP); Yoshiaki Sato, Tokyo (JP)

(73) Assignee: HITACHI, LTD., Tokyo (JP)

(*) Notice: Subject to any disclaimer, the term of this patent is extended or adjusted under 35 U.S.C. 154(b) by 914 days.

(21) Appl. No.: 14/439,819

(22) PCT Filed: Nov. 11, 2013

(86) PCT No.: PCT/JP2013/080373
§ 371 (c)(1),
(2) Date: Apr. 30, 2015

(87) PCT Pub. No.: WO2014/080781
PCT Pub. Date: May 30, 2014

(65) Prior Publication Data
US 2015/0293187 A1    Oct. 15, 2015

(30) Foreign Application Priority Data
Nov. 20, 2012 (JP) .................................. 2012-254112

(51) Int. Cl.
*G01R 33/36* (2006.01)
*G01R 33/28* (2006.01)
(Continued)

(52) U.S. Cl.
CPC ..... *G01R 33/288* (2013.01); *G01R 33/34092* (2013.01); *G01R 33/5608* (2013.01)

(58) Field of Classification Search
CPC ............ G01R 33/288; G01R 33/34092; G01R 33/5608; G01R 33/36; A61B 5/055
See application file for complete search history.

(56) References Cited

U.S. PATENT DOCUMENTS

| | | | |
|---|---|---|---|
| 2005/0057249 A1* | 3/2005 | Dale | G01R 33/54 324/307 |
| 2006/0064002 A1* | 3/2006 | Grist | A61B 5/015 600/410 |

(Continued)

FOREIGN PATENT DOCUMENTS

| | | |
|---|---|---|
| JP | 7-246194 | 9/1995 |
| JP | 11-253416 | 9/1999 |
| WO | WO2010/041706 | 4/2010 |

OTHER PUBLICATIONS

International Search Report in PCT/JP2013/080373.
(Continued)

*Primary Examiner* — Huy Q Phan
*Assistant Examiner* — Adam S Clarke
(74) *Attorney, Agent, or Firm* — Cooper & Dunham LLP

(57) ABSTRACT

A Q value of the RF irradiation coil is easily obtained in a state in which an object is disposed in an MRI apparatus, and an SAR is predicted with high accuracy. For this, an irradiation coil 14a irradiates an object 1 with a high frequency magnetic field pulse in a state in which the object 1 is disposed in an imaging space, and a transmitted voltage and a reflected voltage of the irradiation coil 14a are detected. A Q value of the irradiation coil in a state of the object 1 being disposed is obtained on the basis of the transmitted voltage and the reflected voltage. A specific absorption rate (SAR) in a case of executing an imaging pulse sequence on the object is predicted by using the Q value.

10 Claims, 11 Drawing Sheets

(51) Int. Cl.
*G01R 33/34* (2006.01)
*G01R 33/56* (2006.01)

(56) References Cited

U.S. PATENT DOCUMENTS

| | | | | |
|---|---|---|---|---|
| 2008/0284439 | A1* | 11/2008 | Xu | A61B 5/055 324/322 |
| 2011/0148411 | A1 | 6/2011 | Bottomley et al. | |
| 2011/0181287 | A1* | 7/2011 | Ito | A61B 5/055 324/318 |
| 2012/0256626 | A1* | 10/2012 | Adalsteinsson | G01R 33/5612 324/309 |
| 2013/0063143 | A1* | 3/2013 | Adalsteinsson | G01R 33/5612 324/307 |
| 2013/0285659 | A1* | 10/2013 | Sohn | G01R 33/34092 324/314 |
| 2014/0232401 | A1* | 8/2014 | Takagi | G01R 33/56 324/309 |
| 2015/0268321 | A1* | 9/2015 | Zhai | G01R 33/288 324/309 |
| 2017/0146620 | A1* | 5/2017 | Habara | A61B 5/055 |

OTHER PUBLICATIONS

A. M. El-Sharkawy et al., "A Multi-Channel, High Dynamic Range, Real Time RF Power Deposition Monitor", Proc. Intl. Soc. Mag. Reson. Med., 2011, pp. 496, vol. 19.

B. Gagoski et al., "Flexibly shaped saturation band excitation using 7T parallel transmit system", Proc. Intl. Soc. Mag. Reson. Med., 2011, pp. 4437, vol. 19.

L. Alon et al., "An Automated Method for Subject Specific Global SAR Prediction in Parallel Transmission".

Sukhoon Oh et al., "Thermal Conduction from Coil: Assessment of Effects and Comparison to Simulation", Proc. Intl. Soc. Mag. Reson. Med., 2012, pp. 2934, vol. 20.

Y. Zhu, "In Vivo RF Power and SAR Calibration for Multi-Port RF Transmission", Proc. Intl. Soc. Mag. Reson. Med., 2009, pp. 2585, vol. 17.

Chinese official action dated Dec. 5, 2016 (and partial English translation) in corresponding Chinese Patent Application No. 201380054221.0.

* cited by examiner

FIG. 3

(a) OBJECT REGISTRATION
- NAME
- SEX
- DATE OF BIRTH
- HEIGHT
- WEIGHT
- PART TO BE IMAGED
- IMAGING POSTURE (b) IMAGING CONDITION
- Field of View
- SEQUENCE
- REPETITION TIME
- NUMBER OF CAPTURED IMAGES
- NUMBER OF ADDITIONS (c) SAR INFORMATION
SIX-MINUTE AVERAGE
- WHOLE BODY SAR
- PARTIAL BODY SAR
- HEAD SAR

TEN-SECOND AVERAGE
- WHOLE BODY SAR
- PARTIAL BODY SAR
- HEAD SAR

Q VALUE

MAGNETIC RESONANCE IMAGING APPARATUS AND SAR PREDICTION METHOD

TECHNICAL FIELD

The present invention relates to a magnetic resonance imaging (hereinafter, referred to as "MRI") apparatus which measures a nuclear magnetic resonance (hereinafter, referred to as "NMR") signal from hydrogen, phosphorous, or the like in an object, and generates an image of a density distribution of nuclei, a relaxation time distribution, or the like, and particularly to an apparatus which can reduce a radio frequency absorption amount of an object to a threshold value or less.

BACKGROUND ART

An MRI apparatus measures an NMR signal generated by nuclear spins which form an object, especially, human body tissues, and generates morphology or functions of the head, the abdomen, the limbs, or the like as a two-dimensional or a three-dimensional image. During imaging, radio frequency (RF) pulses for exciting an object, and gradient magnetic field pulses having a phase encoding direction and a frequency encoding direction are applied according to a predetermined imaging pulse sequence. Consequently, an NMR signal emitted by the object is subject to phase encoding and frequency encoding so as to be measured as time-series data. The measured NMR signal is subject to two-dimensional or three-dimensional Fourier transform and is thus reconstructed into an image.

In the MRI apparatus, in order to minimize an influence such as a temperature increase on an object, exerted by the RF pulses, it is necessary to reduce a specific absorption rate (SAR) (an absorption amount of RF per unit mass) to a threshold value or less according to a regulation of the International Electro technical Commission (IEC) (PTL 1). An expression for calculating an SAR is given by the IEC.

In addition, as disclosed in NPL 1, it is known that a Q value of an RF applying device (an irradiation coil) is necessary in order to accurately measure or predict an SAR. The Q value is generally known as a parameter indicating the sharpness of resonance, but the Q value of the RF irradiation coil of the MRI apparatus depends on an internal resistance of an object irradiated with an RF pulse. For this reason, in the related art, a Q value is predicted and used by using an actually measured value of the RF irradiation coil or a region, measured in the past.

CITATION LIST

Patent Literature

[PTL 1] Specification of U.S. Pat. No. 5,916,161 Non Patent Literature
[NPL 1] AKIHIRO ISHIKURO, et al., Comparison of Specific Absorption Ratio Monitoring Values on Various MRI Systems, Japan Society of Radiological Technology 2000; 56 (5): 731 to 736

SUMMARY OF INVENTION

Technical Problem

In order to acquire a reconstructed image with high resolution, an RF pulse having as great an intensity as possible is preferably applied within a range not exceeding a threshold value of an SAR. For this reason, whether or not an imaging pulse sequence to be executed by an MRI apparatus will exceed a threshold value of an SAR in an object to be imaged is preferably obtained with high accuracy. However, since the Q value of the RF irradiation coil required to calculate the SAR changes depending on internal resistance of the object, it is necessary to obtain an actual Q value in a state in which the object to be imaged is disposed in an imaging region, in order to measure the Q value.

In order to measure a Q value of the RF irradiation coil, attachment and detachment of a Q value measurement apparatus are generally necessary but are practically hard to perform for every imaging in the MRI apparatus. On the other hand, a method of measuring a Q value by using a Q value of the irradiation coil measured in the past in a state in which an object to be imaged is disposed is lower than a case of actually measuring a Q value in terms of accuracy.

An object of the present invention is to predict an SAR with high accuracy by easily obtaining a Q value of an RF irradiation coil in a state in which an object is disposed in an MRI apparatus.

Solution to Problem

In the present embodiment, an irradiation coil irradiates an object with a high frequency magnetic field pulse in a state in which the object is disposed in an imaging space, a transmitted voltage and a reflected voltage of the irradiation coil are detected, and a Q value of the irradiation coil in the state in which the object is disposed is obtained on the basis of the transmitted voltage and the reflected voltage. A specific absorption rate (SAR) in a case of executing an imaging pulse sequence on the object is predicted by using the Q value.

Advantageous Effects of Invention

According to the present invention, since a Q value of the RF irradiation coil is easily obtained in a state in which an object is disposed in the MRI apparatus, and an SAR can be predicted with high accuracy, it is possible to set power or the like of an RF pulse to a great value within a range in which the SAR does not exceed a threshold value.

BRIEF DESCRIPTION OF DRAWINGS

FIGS. 3(a) to 3(c) are diagrams illustrating an example of a GUI displayed by the SAR prediction unit 33.

DESCRIPTION OF EMBODIMENTS

Figure 1:
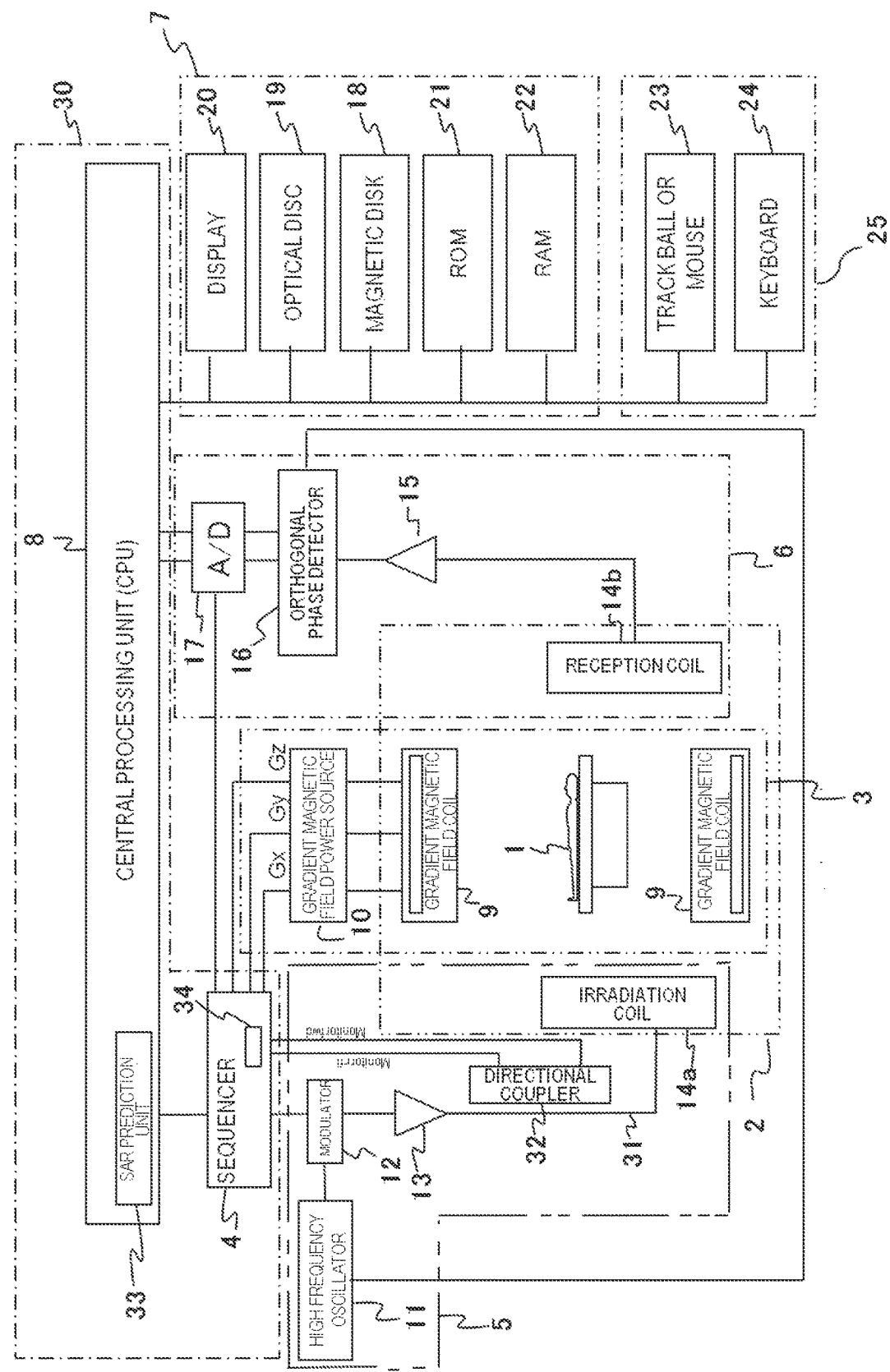
FIG. 1 is a block diagram illustrating an entire configuration of an MRI apparatus according to an embodiment.

An MRI apparatus of the present invention includes a static magnetic field generation section that applies a static magnetic field to an imaging space; a bed on which an object is disposed in the imaging space; a gradient magnetic field coil which applies a gradient magnetic field to the imaging space; an irradiation coil that irradiates the imaging space with a high frequency magnetic field; a reception coil that receives a nuclear magnetic resonance signal generated by the object in the imaging space; and a control section. The control section controls a timing at which the gradient magnetic field is applied from the gradient magnetic field coil and a timing at which the high frequency magnetic field is applied from the irradiation coil according to a predetermined imaging pulse sequence. The control section includes an SAR prediction unit, and predicts a specific absorption rate (SAR) obtained when the imaging pulse sequence is executed on the object, by using a Q value of the irradiation coil.

The SAR prediction unit causes the irradiation coil to irradiate the object with a high frequency magnetic field pulse in a state in which the object is disposed in the imaging space, and detects a transmitted voltage and a reflected voltage of the irradiation coil. The SAR prediction unit obtains a Q value of the irradiation coil in the state in which the object is disposed on the basis of the detected transmitted voltage and the reflected voltage, and predicts the SAR by using the obtained Q value.

As mentioned above, in the present invention, since a high frequency magnetic field pulse is actually applied from the irradiation coil in a state in which the object is disposed in the imaging space, and a transmitted voltage and a reflected voltage are detected, a Q value can be obtained including an influence by internal resistance or the like of the object. Therefore, an SAR can be predicted with high accuracy by using this Q value. In addition, according to this method of obtaining a Q value, a special Q value measurement device is not necessary, and a Q value can be easily obtained.

Hereinafter, an MRI apparatus according to an embodiment of the present invention will be described in detail. In addition, constituent elements having the same functions are given the same reference numerals throughout all the drawings, and repeated description will be omitted.

First, an entire summary of an example of an MRI apparatus according to the present invention will be described with reference to FIG. 1. FIG. 1 is a block diagram illustrating an entire configuration of an example of the MRI apparatus according to the present invention. The MRI apparatus obtains a tomographic image of an object by using an NMR phenomenon, and includes, as illustrated in FIG. 1, a static magnetic field generation system 2; a gradient magnetic field generation system 3; a transmission system 5; a reception system 6; a control section 30; a display/storage section 7; an operation section 25; and a bed for disposing an object 1 in an imaging space.

The control section 30 includes a sequencer 4 and a central processing unit (CPU) 8, and not only controls each section but also performs signal processing so as to perform image reconstruction.

The static magnetic field generation system 2 includes a static magnetic field generation source in order to generate a static magnetic field in an imaging space where a region of the object 1 to be imaged is disposed. As the static magnetic field generation source, a permanent magnet, a normal conducting magnet, or a superconducting magnet is used. A vertical magnetic field type static magnetic field generation source generates uniform static magnetic fields in a direction perpendicular to a body axis of an object, and a horizontal magnetic field type static magnetic field generation source generates uniform static magnetic fields in a body axis direction of the object. In a case of the vertical magnetic field type, the static magnetic field generation source is a pair of magnets which are vertically disposed to oppose each other with an imaging space interposed therebetween.

In a case of the horizontal magnetic field type, the static magnetic field generation source has a cylindrical shape, and an inner space of the cylinder is an imaging space.

The gradient magnetic field generation system 3 includes gradient magnetic field coils 9 which respectively apply gradient magnetic fields Gx, Gy and Gz in three axis directions of X, Y, and Z which are coordinate system (a static coordinate system) of the MRI apparatus, and a gradient magnetic field power source 10 which drives the respectively gradient magnetic field coils 9. The gradient magnetic field power source 10 supplies driving currents to the respective gradient magnetic field coils 9 in response to a command from the sequencer 4.

Consequently, the gradient magnetic field generation system 3 applies a slice direction gradient magnetic field pulse (Gs) in a direction perpendicular to a slice surface (imaging cross-section) during imaging so as to set a slice surface in the object 1, and applies a phase encoding direction gradient magnetic field pulse (Gp) and a frequency encoding direction gradient magnetic field pulse (Gf) in two directions which are perpendicular to the slice surface and are perpendicular to each other so as to add position information in each direction to an echo signal.

The transmission system 5 includes a high frequency oscillator 11; a modulator 12; a high frequency amplifier 13; and an irradiation coil 14a. The high frequency oscillator 11 generates a high frequency signal, and the high frequency signal is modulated by the modulator 12 so as to be amplified by the high frequency amplifier 13 and is then supplied to the high frequency coil (irradiation coil) 14a via a signal line 31. The irradiation coil 14a is supplied with the high frequency signal and irradiates the object 1 in the imaging space with an RF pulse so as to cause nuclear magnetic resonance in nuclear spins of atoms forming a biotissue of the object 1.

The reception system 6 includes a reception side high frequency coil (reception coil) 14b; a signal amplifier 15; an orthogonal phase detector 16; and an A/D converter 17. With this configuration, the reception system 6 detects an echo signal (NMR signal) emitted due to the nuclear magnetic resonance of the nuclear spins forming the biotissue of the object 1. Specifically, the NMR signal (echo signal) emitted by the object 1 excited by the RF pulse applied from the transmission side high frequency coil 14a is detected by the reception coil 14b disposed near the object 1. The received signal is amplified by the signal amplifier 15 and is then divided into signals in two systems perpendicular to each other by the orthogonal phase detector 16 at timing set in response to a command from the sequencer 4. The signals are respectively converted into digital amounts by the A/D converter 17 and are then sent to the control section 30 which is also used as a signal processing system.

The sequencer 4 of the control section 30 outputs signals for commanding operations to the modulator 12 of the transmission system 5, the gradient magnetic field power source 10 of the gradient magnetic field generation system 3, and the A/D converter 17 of the reception system, and thus an RF pulse and a gradient magnetic field pulse are applied to the object 1 in the imaging space at timing which is set in a predetermined imaging pulse sequence. In addition, the reception system 6 is controlled to receive an echo signal at a predetermined timing. The CPU 8 of the control section 30 executes an imaging program stored in an internal memory and thus controls an operation of the sequencer 4 so that a predetermined imaging pulse sequence is executed.

In addition, the CPU 8 of the control section 30 executes a signal processing program stored in the internal memory and thus operates as a signal processing system so as to perform control related to various data processes, display and preservation of processed results, and the like. If the CPU 8 receives data of the NMR signal from the reception system 6, the CPU performs a process such as image reconstruction through signal processing, so as to obtain an image of the object 1, and displays the image on a display 20 of the display/storage section 7 and stores the image on a magnetic disk of an external storage device.

In the present embodiment, the CPU 8 of the control section 30 executes a predefined SAR prediction program and thus functions as a SAR prediction unit 33, as will be described later.

In addition, a directional coupler 32 is disposed in the signal line 31 of the irradiation coil 14a. A voltage detection unit 34 which detects a part of a transmitted signal and a part of a reflected signal, separated by the directional coupler 32, is disposed in the sequencer 4. Consequently, the voltage detection unit 34 can detect a voltage (transmitted voltage) of the transmitted signal supplied to the irradiation coil 14a, and a voltage (reflected voltage) of the reflected signal which is reflected due to impedance mismatching between the irradiation coil 14a and the object 1.

The SAR prediction unit 33 causes the irradiation coil 14a to irradiate the object 1 with a predefined high frequency magnetic field pulse in a state in which the object is disposed in the imaging space before imaging the object, and causes the voltage detection unit 34 to detect a voltage transmitted to and a voltage reflected from the irradiation coil 14a. A Q value of the irradiation coil 14a in a state in which the object is disposed is obtained on the basis of the detected transmitted voltage and reflected voltage, and an SAR of an imaging pulse sequence which is executed from now on is predicted by using the obtained Q value. Consequently, in a case where a prediction value of an SAR exceeds a threshold value defined by the IEC, conditions of the imaging pulse sequence can be changed.

The display/storage section 7 includes external storage devices such as an optical disc 19 and a magnetic disk 18, and the display 20 such as a CRT. The operation section 25 inputs various control information pieces regarding the MRI apparatus or control information regarding processes performed by the display/storage section 7, and includes a track ball or a mouse 23, and a keyboard 24. The operation section 25 is disposed near the display 20, and an operator controls various processes in the MRI apparatus in an interactive manner via the operation section 25 while viewing the display 20.

In addition, the gradient magnetic field coil 9 and the irradiation coil 14a are disposed at a position closer to the object 1 than to the static magnetic field generation source. The reception coil 14b is provided so as to oppose or to surround the object 1.

Currently, an imaging target nuclide of the MRI apparatus is a hydrogen atomic nucleus (proton) which is a main constituent substance of an object as a nuclide which has been widespread in a clinical manner. Information regarding a spatial distribution of proton densities or a spatial distribution of excitation state relaxation times is generated as an image, and thus morphology or functions of the head, the abdomen, the limbs, and the like of the human body are imaged in a two-dimensional or three-dimensional manner.

Hereinafter, an operation of the SAR prediction unit 33 will be described in detail as first to fourth embodiments.

First Embodiment

In a first embodiment, the SAR prediction unit 33 causes the irradiation coil 14a to apply a high frequency magnetic field pulse with a predetermined frequency as a predefined high frequency magnetic field pulse, then obtains a standing wave ratio $V_{SWR}$ on the basis of a transmitted voltage and a reflected voltage of the irradiation coil 14a, and obtains a Q value on the basis of the standing wave ratio $V_{SWR}$. For example, the SAR prediction unit 33 may obtain a Q value corresponding to an obtained standing wave ratio $V_{SWR}$ from a relationship between the standing wave ratio $V_{SWR}$ and the Q value, which is obtained in advance.

An operation of the SAR prediction unit 33 of the first embodiment will be described more in detail with reference to a flowchart of FIG. 2 or the like. The SAR prediction unit 33 obtains a Q value of the irradiation coil 14a with high accuracy in a state in which the object 1 is disposed in the imaging space so as to predict an SAR of an imaging pulse sequence to be executed, and changes conditions of the imaging pulse sequence in a case where the predicted SAR exceeds a threshold value (an IEC reference value). In addition, an SAR is actually measured during execution of the imaging pulse sequence, and the imaging pulse sequence is stopped in a case where the measured SAR exceeds the IEC reference value.

First, the SAR prediction unit 33 displays an object registration GUI illustrated in FIG. 3(a) on the display 20, and receives inputting of object information (the name, a sex, the date of object's birth, a height, and a weight), a region to be imaged (the head, the chest, the abdomen, or the like), and an imaging posture (lying face down, lying face up, or the like), from an operator via the operation section 25 (step 301).

Next, the operator places the object 1 on a bed and disposes the region to be imaged in the imaging space of the MRI apparatus. The SAR prediction unit 33 causes the object 1 in the imaging space to be irradiated with a predetermined RF pulse (a reference RF pulse) which is predefined so as to obtain a transmitted voltage of a transmitted signal and a reflected voltage of a reflected signal of the irradiation coil 14a and thus to obtain a Q value, and obtains an RF absorption amount of the object 1 relative to the reference RF pulse on the basis of the obtained Q value (step 302). A specific operation in step 302 will be described later.

Next, the SAR prediction unit 33 obtains a weight (partial weight) of a part (region) of the object 1 present in the irradiation region of the irradiation coil 14a through calculation (step 303). Specifically, an internal memory of the SAR prediction unit 33 stores data indicating a proportion of a part of the entire object 1 located in the irradiation region of the irradiation coil 14a for each region to be imaged of the object 1 and for each region specified by an imaging posture. For example, if a region to be imaged is the chest, about 30% of the overall weight is present in the irradiation region of the irradiation coil 14a. The SAR prediction unit 33 reads a proportion of the region to be imaged input by the operator in step 301 and a region specified by the imaging posture relative to the overall weight of the object 1, from the internal memory, and obtains a partial weight by multiplying the weight input by the operator in step 301 by the proportion.

Next, the SAR prediction unit 33 receives selection of one or more types of imaging pulse sequences (a spin echo method, a gradient echo method, and the like) used for imaging the object 1 from the operator, and receives specific settings of parameters for each type from the operator (step 304). Specifically, the SAR prediction unit 33 displays an imaging sequence condition GUI of FIG. 3(b) on the display 20, and receives a field of view, selection of any one of a plurality of predefined sequences, repeated time (TR), the number of captured images, the number of additions of a selected sequence (the number of additions (the number of measurements) of an echo signal for each phase encoding), and the like. Consequently, irradiation intensity of an RF pulse, the number of irradiations, an irradiation interval, and the like in the imaging pulse sequence are determined.

Next, the SAR prediction unit 33 obtains an SAR through calculation by using the reference RF pulse in step 302, a waveform ratio (the following Equation (1)) of the RF pulse of the imaging pulse sequence set in step 304, the RF absorption amount of the object 1 obtained through irradiation with the reference RF pulse in step 302, and a period of execution time of the imaging pulse sequence set in step 304, and the irradiation intensity, the number of irradiations, and the irradiation interval of the RF pulse, set in step 304 (step 305). Here, a six-minute average SAR (a whole-body SAR, a partial-body SAR, a head SAR) and a ten-second average SAR (a whole-body SAR, a partial-body SAR, a head SAR) are obtained.

$$RfWaveRation_1 = \frac{\int F_1(t')dt'}{\int F_0(t'')dt''} \quad (1)$$

Here, in the above Equation (1), $F_1(t)$ indicates a waveform of all RF pulses applied in the imaging pulse sequence, and $F_0(t)$ indicates a waveform of the reference RF pulse applied in step 302.

If the waveform ratio obtained from Equation (1) is multiplied by the RF absorption amount of the object 1 obtained in step 302, an RF absorption amount of the object 1 is obtained. If time averages of the RF absorption amount for six minutes and ten seconds are obtained and are divided by the weight of the whole body, a six-minute average whole body SAR and a ten-second average whole body SAR can be obtained. In addition, if the whole body SAR is multiplied by the proportion of the partial weight to the whole body weight obtained in step 303, a partial body SAR can be obtained. If time averages of the partial body SAR for six minutes and ten seconds are obtained, a six-minute average partial body SAR and a ten-second average partial body SAR can be obtained.

The head SAR is obtained by dividing a result by the weight of the head, the result being obtained by multiplying the RF absorption amount by a proportion of an absorption amount of the head. If time averages of the head SAR for six minutes and ten seconds are obtained, a six-minute average head SAR and a ten-second average head SAR can be obtained.

The SAR prediction unit 33 displays each SAR value obtained in step 305 on an SAR and Q value display GUI (FIG. 3(c)) of the display 20 along with the Q value obtained in step 302. The operator can understand each SAR and the Q value from the GUI of FIG. 3(c).

The SAR prediction unit 33 compares the respective obtained (predicted) SARs and reference SARs defined by the IEC. In a case where any one of the predicted SARs exceeds the reference SAR, the imaging pulse sequence cannot be executed in this state, and thus the flow returns to step 304, and then the SAR prediction unit receives resetting (changing of a parameter or setting of a period of standby time) of conditions of the imaging pulse sequence from the operator (step 305). On the other hand, in a case where each predicted SAR is equal to or lower than the reference SAR, the flow proceeds to step 307.

The SAR prediction unit 33 instructs the sequencer to execute the imaging pulse sequence set in step 304 (step 307). Consequently, the sequencer 4 executes the imaging pulse sequence by controlling the transmission system 5, the gradient magnetic field generation system 3, and the reception system 6. During the time, the SAR prediction unit 33 receives a transmitted voltage $V_{fwd}$ and a reflected voltage $V_{rfl}$ of the irradiation coil 14a of the transmission system 5 via the directional coupler 32 and the voltage detection unit 34 of the sequencer 4, and obtains a RF absorption amount $P_{object}$ of the object according to Equations (2) and (3).

$$P_{object} = P_c \times \left(1 - \frac{Q}{Q'}\right) \quad (2)$$

$$P_c = P_{fwd} - P_{rfl} \quad (3)$$

Here, $P_{fwd}$ is obtained on the basis of $V_{fwd}$ by using a calculation equation given by the IEC. $P_{rfl}$ is also obtained on the basis of $V_{rfl}$ in the same manner. The Q value obtained in step 302 in a state in which the object 1 is disposed in the imaging space is used as Q. Q' is a Q value measured in a state in which the object 1 is not disposed, and a value obtained in advance is used.

Time averages for six minutes and ten seconds are obtained in relation to the RF absorption amount $P_{object}$ during the execution of the imaging pulse sequence, obtained by using Equations (2) and (3), and are respectively divided by the whole body weight, and thus an actually measured value of the six-minute average whole body SAR and an actually measured value of the ten-second average whole body SAR are obtained. In addition, if the whole body SAR is multiplied by the proportion of the partial body weight to the whole body weight, obtained in step 303, an actually measured value of the partial body SAR is obtained. Time averages thereof for six minutes and ten seconds are obtained, and thus an actually measured value of the six-minute average partial body SAR and an actually measured value of the ten-second average partial body SAR are obtained. The head SAR is obtained by obtaining time averages of the RF absorption amount $P_{object}$ for six minutes and ten seconds and by dividing a result by the head weight, the result being obtained by multiplying the time averages by a proportion of an absorption amount of the head.

The actually measured values of the six-minute average whole body SAR, the ten-second average whole body SAR, the six-minute average partial body SAR, and the ten-second average partial body SAR, and the head SAR are compared with the IEC reference values, and if any one of the SARs exceeds the IEC reference value, the sequencer 4 is instructed to stop the imaging pulse sequence (step 307). Consequently, the imaging pulse sequence is forced to be stopped, and thus an actually measured value of the SAR does not exceed the SAR reference value.

In a case where the same object 1 is set to be imaged in a plurality of imaging pulse sequences in step 304, the flow returns to step 304, and steps 304 to 307 are repeatedly executed until all the imaging pulse sequences are finished. The CPU 8 performs signal processing on an NMR signal acquired through the execution of the imaging pulse sequence so as to reconstruct an MRI image of the object 1.

Figure 4:
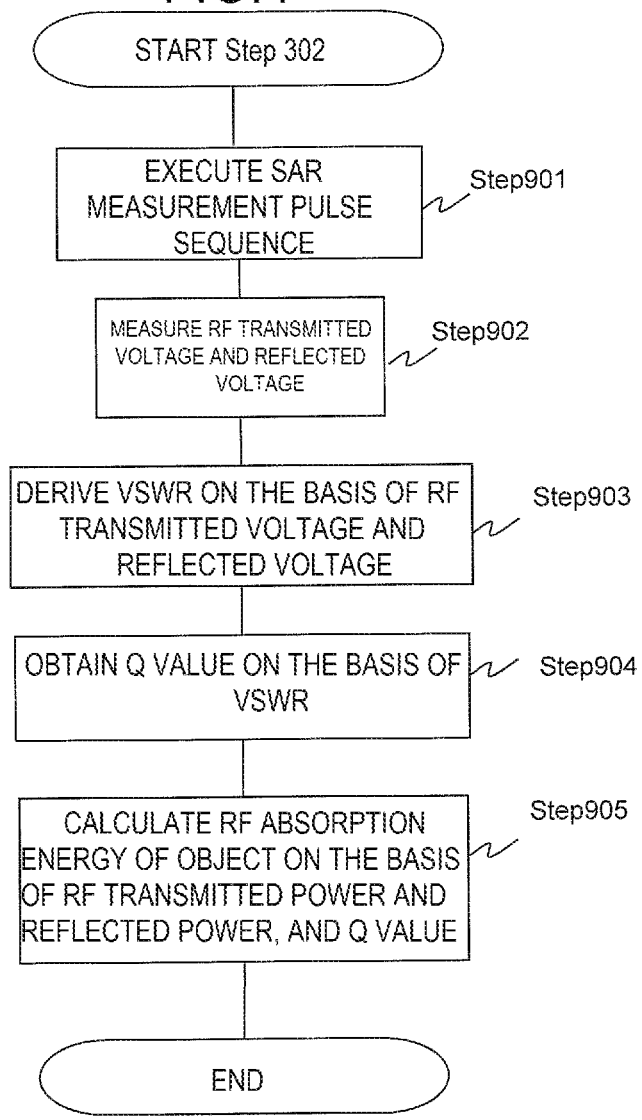
FIG. 4 is a flowchart illustrating details of step 302 of FIG. 2.
Figure 5:
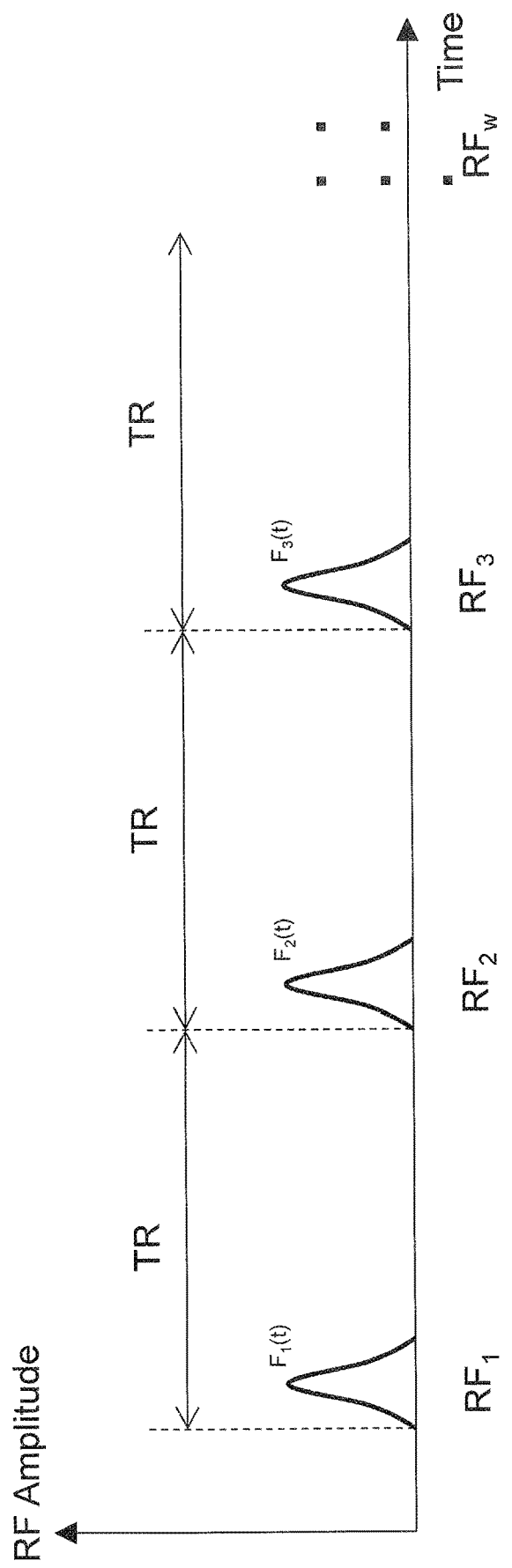
FIG. 5 is a flowchart illustrating a pulse sequence for measuring a SAR in the first embodiment.

Here, the above-described step 302 will be described in detail with reference to FIG. 4. The operator places the object 1 on a bed and disposes the region to be imaged in the imaging space of the MRI apparatus. The SAR prediction unit 33 executes a SAR measurement pulse sequence illustrated in FIG. 5 (step 901). In other words, the object 1 in the imaging space is irradiated by the irradiation coil 14a of the transmission system 5 with predetermined RF pulses (reference RF pulses) $RF_1$, $RF_2$, $RF_3$, ... at intervals of predetermined TR by a predetermined number of times. A frequency of the reference RF pulses $RF_1$, $RF_2$, $RF_3$, ... is set to a resonance frequency of water, and the amplitude thereof is set to a predefined amplitude which has been confirmed not to exceed the SAR reference value of the IEC even if the SAR measurement pulse sequence is executed in most of objects.

During irradiation, parts of a transmitted wave and a reflected wave of the irradiation coil 14a are separated by the directional coupler 32 and are detected by the voltage detection unit 34 of the sequencer 4, and thus a transmitted voltage $V_{fwd}$ and a reflected voltage $V_{rfl}$ of the irradiation coil 14a are detected (step 902).

The SAR prediction unit 33 obtains a voltage standing wave ratio $V_{SWR}$ by using Equations (4) and (5) (step 903). Here, ρ indicates a reflection coefficient.

$$\rho = V_{rfl}/V_{fwd} \quad (4)$$

$$V_{SWR} = (1+\rho)/(1-\rho) \quad (5)$$

Figure 6:
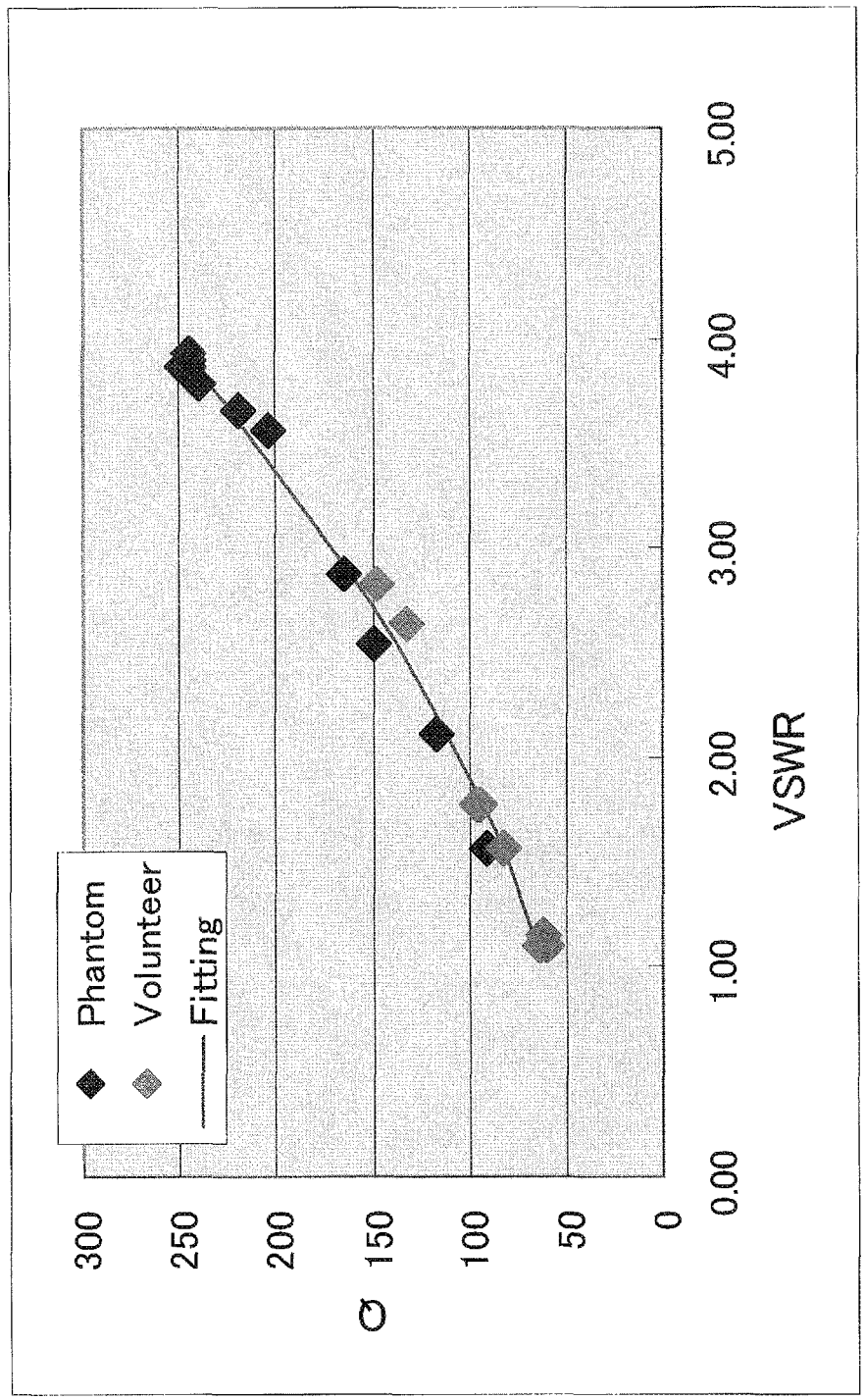
FIG. 6 is a graph illustrating a relationship between a voltage standing wave ratio $V_{SWR}$ and a Q value, used in the first embodiment.

The SAR prediction unit 33 refers to a function, a table, a graph (FIG. 6), or the like indicating a relationship between the voltage standing wave ratio $V_{SWR}$ and a Q value, stored in the internal memory in advance, so as to obtain a Q value corresponding to the voltage standing wave ratio $V_{SWR}$ obtained in step 903 (step 904). This Q value is a Q value obtained in a state in which the object 1 is disposed in the imaging space. In addition, as is clear from the graph of FIG. 6, the voltage standing wave ratio $V_{SWR}$ and the Q value have a relationship of a predetermined function, and this function may be obtained by using a phantom object or a volunteer object.

Next, the SAR prediction unit 33 obtains the RF absorption amount $P_{object}$ of the object when the reference RF pulse is applied on the basis of the Q value obtained in step 904 and the above-described Equations (2) and (3). Here, $P_{fwd}$ is obtained on the basis of $V_{fwd}$ by using a calculation equation given by the IEC (step 905).

$P_{rfl}$ is also obtained on the basis of $V_{rfl}$ in the same manner. Q' is a Q value measured in a state in which the object 1 is not disposed, and a value obtained in advance is used.

As mentioned above, in the first embodiment, since a Q value of the RF irradiation coil 14a in a state in which the object is disposed in the imaging space of the MRI apparatus can be obtained by using the reference RF pulse in step 302, it is possible to predict an SAR in an actual imaging pulse sequence with high accuracy by using this Q value (steps 305 and 306). Therefore, the intensity of an RF pulse in an actual imaging pulse sequence can be set to a large value within a range in which an SAR does not exceed the reference SAR, and thus it is possible to reconstruct a high resolution MRI image.

In addition, according to the present invention, it is possible to obtain a Q value of the irradiation coil 14a corresponding to the body type of the object 1 or a relative position between the object 1 and the apparatus. By the use of the Q value, a partial weight or an RF consumption amount in the coil used for calculation of an SAR can be obtained, and thus it is possible to accurately and simply monitor and restrict an SAR. Consequently, an imaging condition is changed such that an SAR has a low value in order to prevent an SAR during actual imaging from exceeding a threshold value due to errors of a predicted value of an SAR, but this is not required in the present invention, and it is possible to minimize a reduction in throughput during examination (imaging).

In addition, in the present embodiment, a value measured in advance is used as the Q' value in Equation (2), but if step 302 is executed not only in a state in which the object 1 is disposed in the imaging space but also in a state in which the object 1 is not disposed therein, a Q' value as well as a Q value can be measured.

Second Embodiment

A second embodiment will be described. In the second embodiment, the SAR prediction unit 33 irradiates the object with a high frequency magnetic field pulse having a predetermined frequency different from a high frequency magnetic field pulse for obtaining a Q value. In addition, transmitted power and reflected power are obtained on the basis of a transmitted voltage and a reflected voltage of the irradiation coil 14a, and an SAR is predicted by using a difference therebetween and the Q value.

Figure 2:
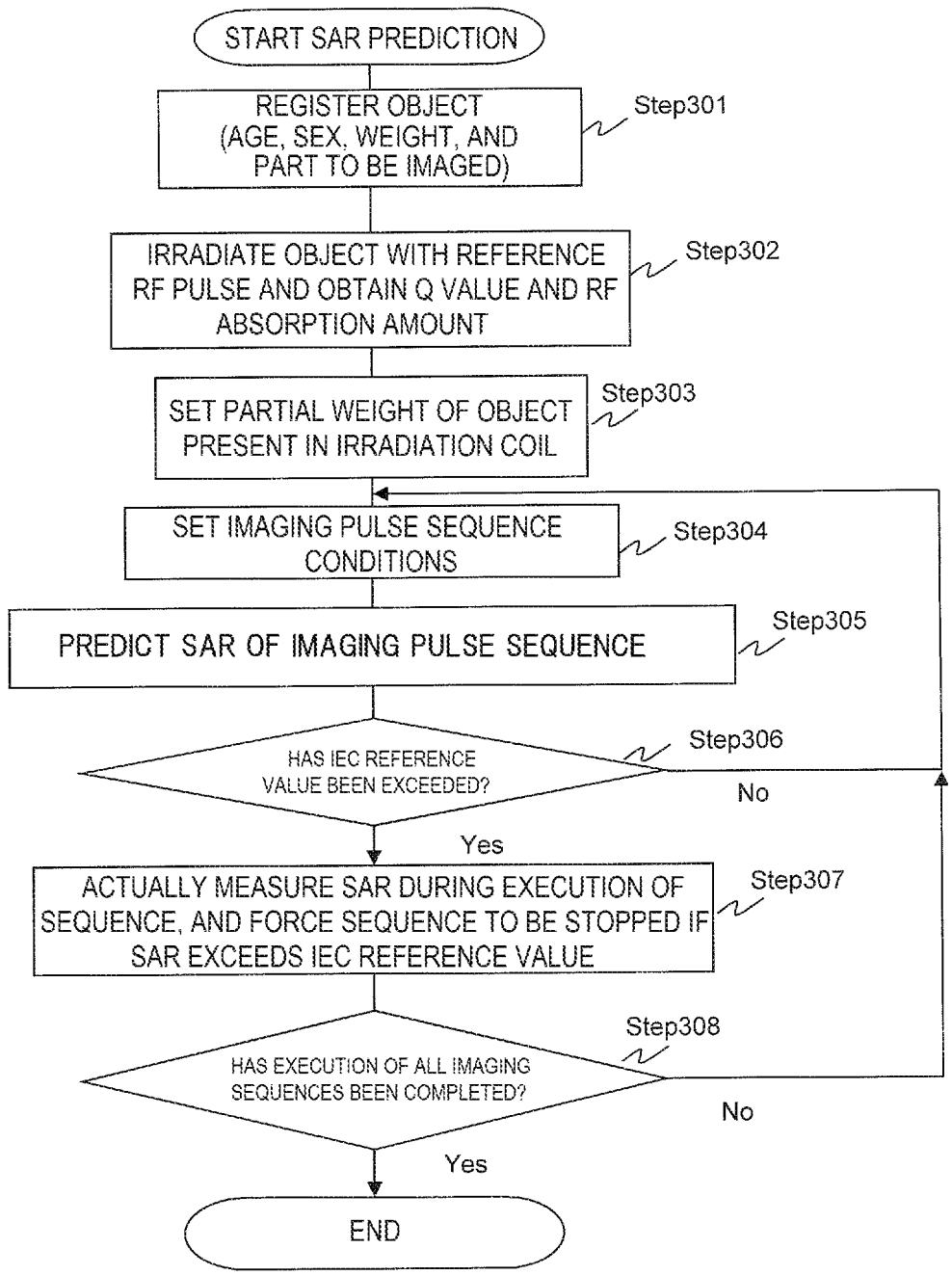
FIG. 2 is a flowchart illustrating an operation of an SAR prediction unit 33 according to a first embodiment.
Figure 7:
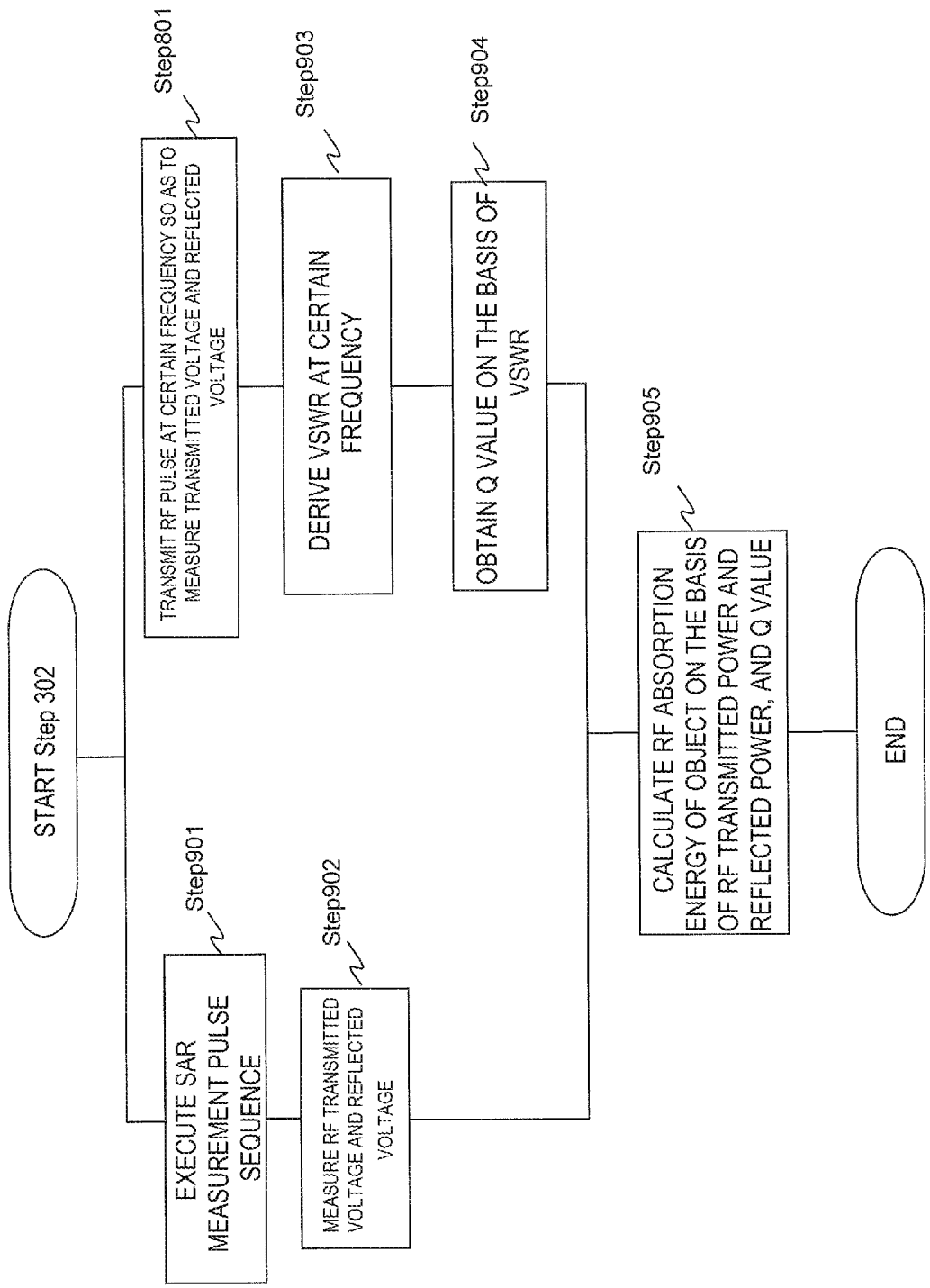
FIG. 7 is a flowchart illustrating an operation of step 302 of the SAR prediction unit 33 in a second embodiment.

Specifically, in the second embodiment, a flow illustrated in FIG. 7 is executed as step 302 of FIG. 2. Other configurations are the same as those in the first embodiment, and thus description thereof will be omitted.

In the flow illustrated in FIG. 7, an SAR measurement pulse sequence is executed in step 801 separately from step 901. An SAR measurement pulse sequence executed in step 901 may or may not be the same as the SAR measurement pulse sequence executed in step 801.

In step 801, $V_{fwd}$ and $V_{rfl}$ used in step 903 are measured, and a voltage standing wave ratio $V_{SWR}$ is obtained. In step 905, Pc is obtained according to Equation (3) by using $P_{fwd}$ and $P_{rfl}$ which are obtained on the basis of a transmitted voltage $V_{fwd}$ and a reflected voltage $V_{rfl}$ measured in step 902. As a Q value, a Q value is used which is obtained on the basis of a transmitted voltage $V_{fwd}$ and a reflected voltage $V_{rfl}$ measured in step 801.

Consequently, in steps 901 and 801, conditions can be changed not only by executing different SAR measurement pulse sequences but also by executing the same SAR measurement pulse sequence. For example, frequencies of an applied reference RF pulse may be set to different frequencies in steps 901 and 801. Other configurations are the same as those in the flow of FIG. 4 in the first embodiment.

Third Embodiment

A third embodiment will be described. In the third embodiment, the SAR prediction unit 33 applies a predefined high frequency magnetic field pulse for multiple times at different frequencies, and detects a transmitted voltage and a reflected voltage of the irradiation coil 14a for each irradiation. Impedances are obtained on the basis of the transmitted voltage and the reflected voltage, and a Q value is obtained by using the maximum value of the impedances.

Figure 8:
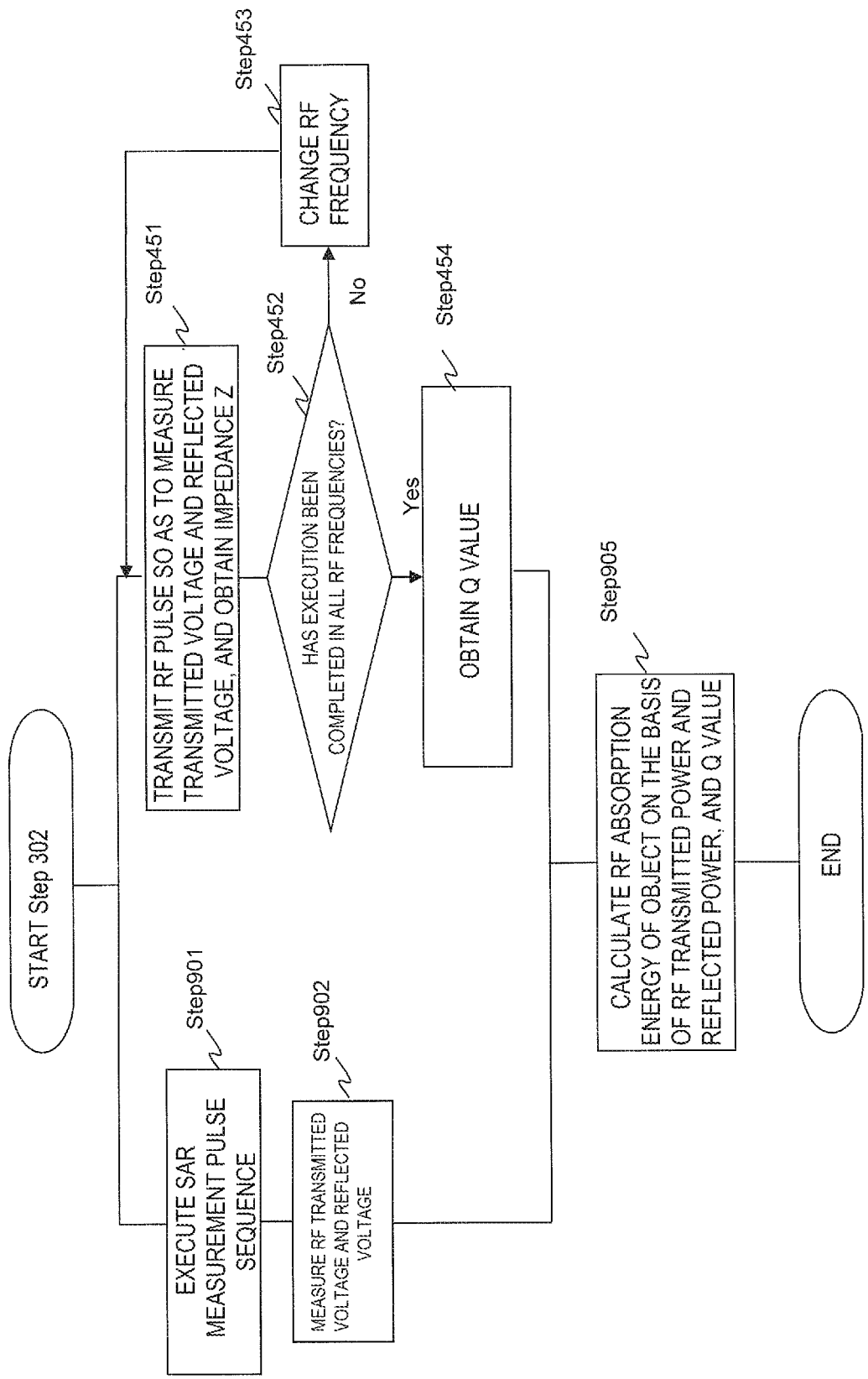
FIG. 8 is a flowchart illustrating an operation of step 302 of the SAR prediction unit 33 in a third embodiment.

Specifically, in the third embodiment, a flow illustrated in FIG. 8 is executed as step 302 of FIG. 2. Other configurations are the same as those in the first embodiment, and thus description thereof will be omitted.

In the flow illustrated in FIG. 8, the present embodiment is different from the first embodiment in that steps 451 to 454 are executed in order to obtain a Q value.

The SAR prediction unit 33 applies a reference RF pulse in step 451 of FIG. 8 in the same manner as in the SAR measurement pulse sequence of step 901, and thus measures a transmitted voltage $V_{fwd}$ and a reflected voltage $V_{rfl}$. An impedance Z is obtained by using the measured transmitted voltage $V_{fwd}$ and reflected voltage $V_{rfl}$, and Equation (6). Here, $\rho$ indicates a reflection coefficient shown in Equation (4). $Z_0$ indicates a characteristic impedance of a transmission line.

$$\rho = V_{rfl}/V_{fwd} \quad (4)$$

$$\frac{|Z - Z_0|}{|Z + Z_0|} = \rho \quad (6)$$

SAR prediction unit 33 repeatedly executes step 451 while changing a frequency f of the reference RF pulse within a predefined range (steps 452 and 453).

Figure 9:
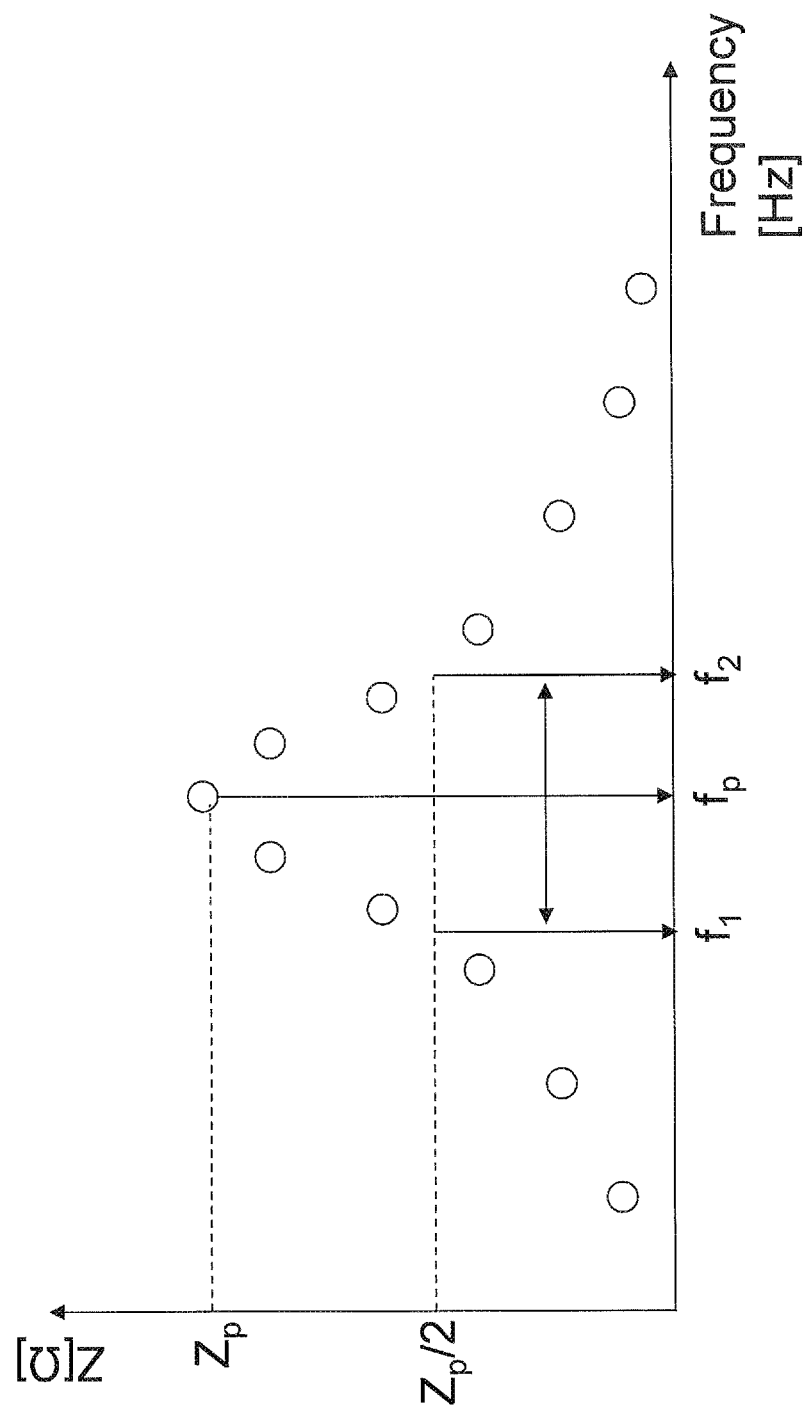
FIG. 9 is a graph illustrating a relationship between an impedance Z obtained by the SAR prediction unit 33 and a frequency in the third embodiment.

Consequently, as illustrated in FIG. 9, a relationship between the frequency f of the reference RF pulse and the impedance Z can be obtained. The SAR prediction unit 33 obtains a frequency fp at which the impedance Z becomes a peak value Zp and frequencies f1 and f2 at which the impedance becomes a half of the peak value Zp on the basis of the relationship, and obtains a Q value according to Equation (7) (step 454).

$$Q = \frac{f_p}{f_2 - f_1} \quad (7)$$

In step 905, as $P_{fwd}$ and $P_{rfl}$ used when obtaining Pc according to Equation (3), values which are obtained on the basis of the transmitted voltage $V_{fwd}$ and the reflected voltage $V_{rfl}$ measured in step 902 are used, and, as a Q value, the value obtained in step 454 is used.

The third embodiment is advantageous in that a function indicating a relationship between a Q value and a certain parameter is not required to be obtained in advance in order to obtain a Q value. In addition, a Q value can be obtained on the basis of an actually measured value without depending on the reliability of a function.

Other configurations are the same as those in the first embodiment, and thus description thereof will be omitted.

Fourth Embodiment

A fourth embodiment will be described. In the fourth embodiment, the SAR prediction unit 33 obtains a Q value corresponding to the impedance maximum value by using a relationship, obtained in advance, between the impedance maximum value and a Q value.

Figure 10:
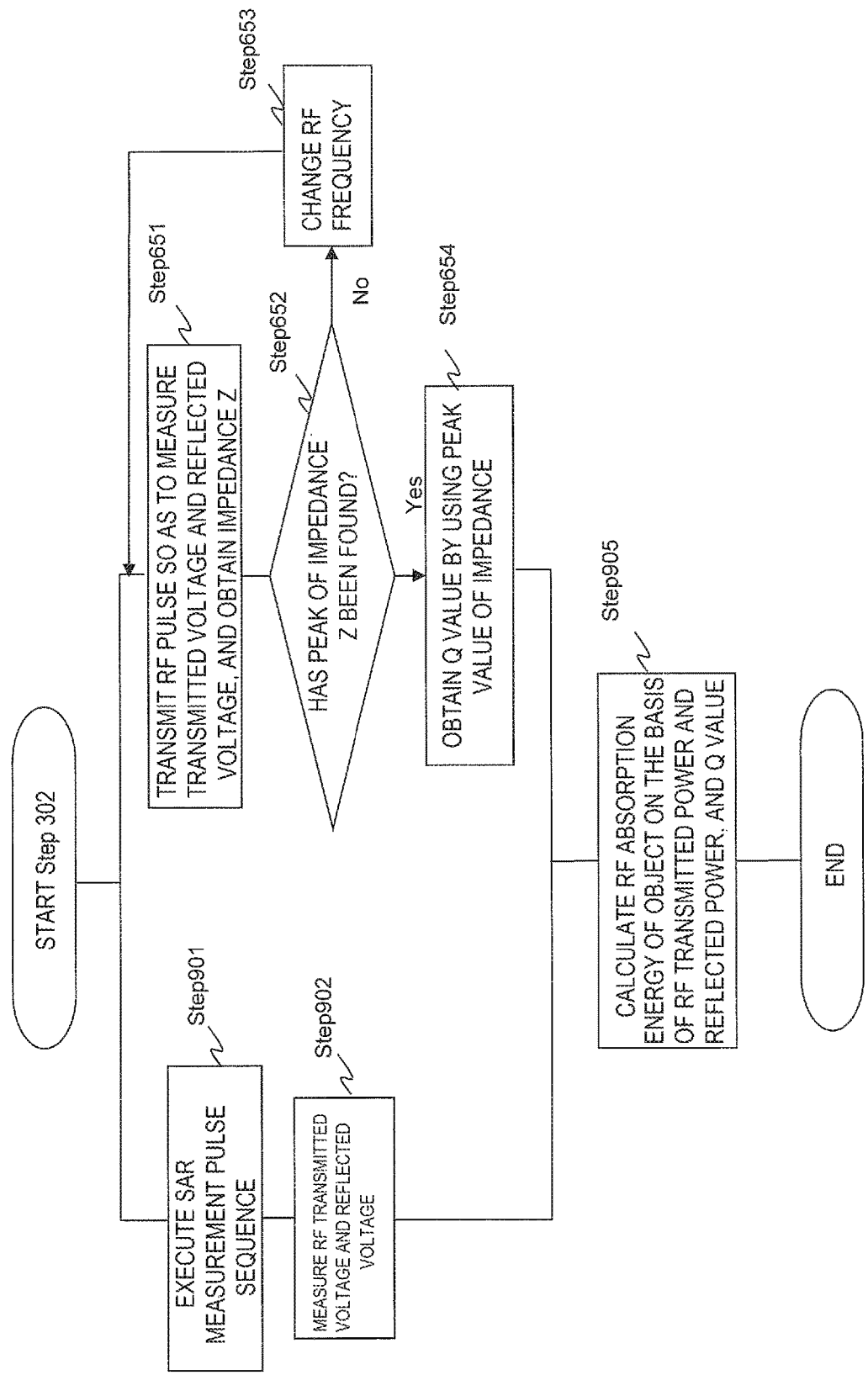
FIG. 10 is a flowchart illustrating an operation of step 302 of the SAR prediction unit 33 in a fourth embodiment.

Specifically, in the fourth embodiment, a flow of FIG. 10 is executed as step 302 of FIG. 2. Other configurations are the same as those in the first embodiment, and thus description thereof will be omitted.

In the flow illustrated in FIG. 10, the present embodiment is different from the first embodiment in that steps 651 to 654 are executed in order to obtain a Q value.

In step 651 of FIG. 10, in the same manner as in step 451 of the third embodiment, the SAR prediction unit 33 executes an SAR measurement pulse sequence, and thus measures a transmitted voltage $V_{fwd}$ and a reflected voltage $V_{rfl}$. An impedance Z is obtained by using the measured transmitted voltage $V_{fwd}$ and reflected voltage $V_{rfl}$, and Equation (6).

In steps 652 and 653, step 451 is repeatedly executed while changing frequencies until a peak value Zp of the impedance Z is found.

Figure 11:
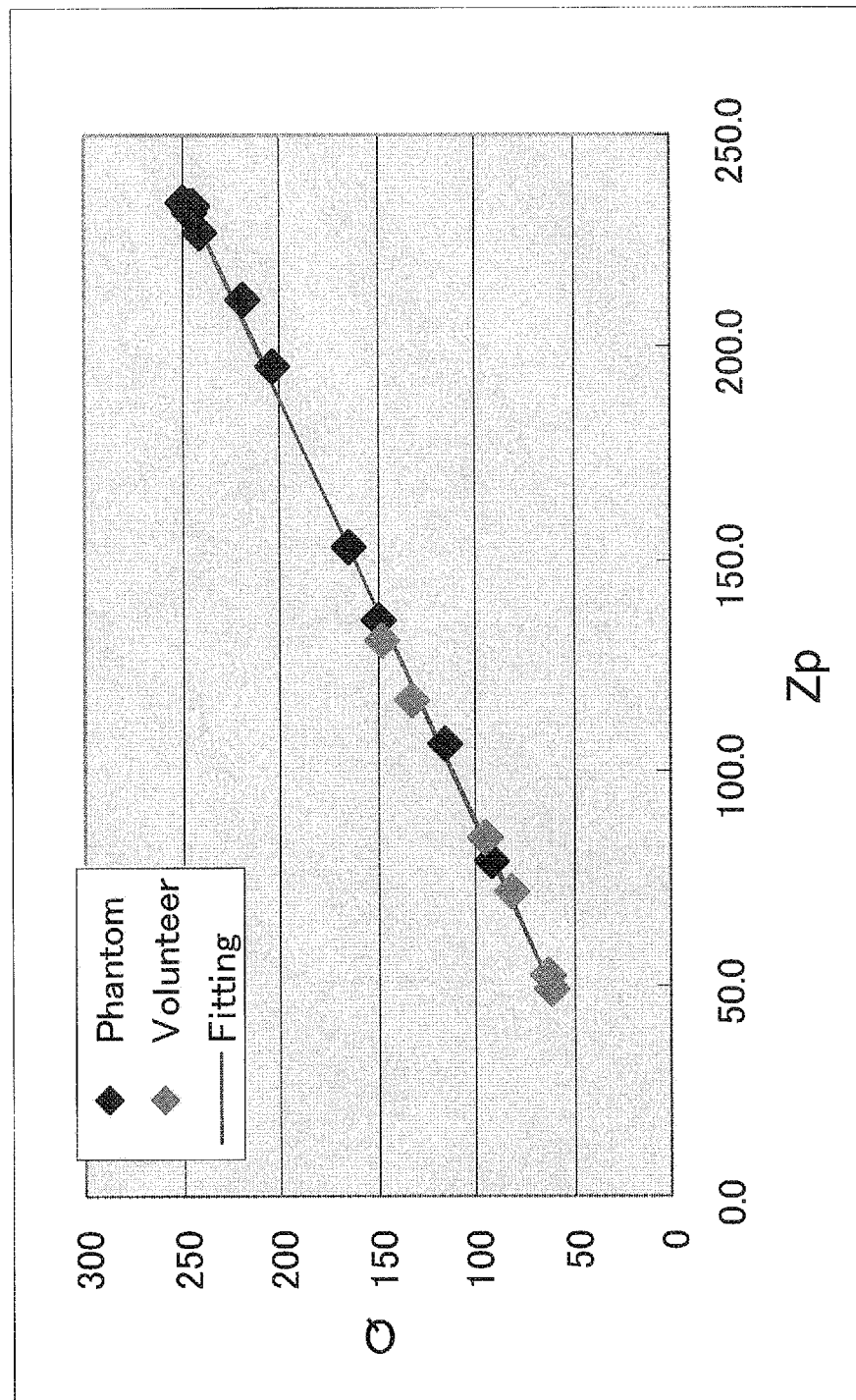
FIG. 11 is a graph illustrating a relationship between a maximum value Zp of an impedance used by the SAR prediction unit 33 and a Q value in the fourth embodiment.

In step 654, a Q value corresponding to the peak value Zp obtained in step 652 is obtained on the basis of a function (an equation, a table, or a graph) (FIG. 11) indicating a relationship between an impedance peak value Zp and a Q value, stored in the internal memory of the SAR prediction unit 33 and obtained in advance.

In step 905, as $P_{fwd}$ and $P_{rfl}$ used when obtaining $P_C$ according to Equation (3), values which are obtained on the basis of the transmitted voltage $V_{fwd}$ and the reflected voltage $V_{rfl}$ measured in step 902 are used, and, as a Q value, the value obtained in step 654 is used.

In the fourth embodiment, since a frequency may be changed in an extent of the peak value Zp being found in step 652, a range in which a frequency is changed in step 651 can be narrowed, and thus a Q value can be obtained in a shorter period of time than in the third embodiment.

Other configurations are the same as those in the first embodiment, and thus description thereof will be omitted.

REFERENCE SIGNS LIST

1 OBJECT, 2 STATIC MAGNETIC FIELD GENERATION SYSTEM, 3 GRADIENT MAGNETIC FIELD GENERATION SYSTEM, 4 SEQUENCER, 5 TRANSMISSION SYSTEM, 6 RECEPTION SYSTEM, 7 DISPLAY/STORAGE SECTION, 8 CENTRAL PROCESSING UNIT (CPU), 9 GRADIENT MAGNETIC FIELD COIL, 10 GRADIENT MAGNETIC FIELD POWER SOURCE, 11 HIGH FREQUENCY OSCILLATOR, 12 MODULATOR, 13 HIGH FREQUENCY AMPLIFIER, 14a HIGH FREQUENCY COIL (IRRADIATION COIL), 14b HIGH FREQUENCY COIL (RECEPTION COIL), 15 SIGNAL AMPLIFIER, 16 ORTHOGONAL PHASE DETECTOR, 17 A/D CONVERTER, 18 MAGNETIC DISK, 19 OPTICAL DISC, 10 DISPLAY, 21 ROM, 22 RAM, 23 TRACK BALL OR MOUSE, 24 KEYBOARD, 30 CONTROL SECTION, 31 SIGNAL LINE, 32 DIRECTIONAL COUPLER, 33 SAR PREDICTION UNIT, 34 VOLTAGE DETECTION UNIT

The invention claimed is:

1. A magnetic resonance imaging apparatus comprising:
a static magnetic field generation section that applies a static magnetic field to an imaging space;
a bed on which an object is disposed in the imaging space;

a gradient magnetic field coil that applies a gradient magnetic field to the imaging space;
an irradiation coil that irradiates the imaging space with a high frequency magnetic field;
a reception coil that receives a nuclear magnetic resonance signal generated by the object in the imaging space; and
a control section that controls a timing at which the gradient magnetic field is applied from the gradient magnetic field coil and a timing at which the high frequency magnetic field is applied from the irradiation coil according to a predetermined imaging pulse sequence,
wherein the control section includes a specific absorption rate (SAR) prediction unit that predicts a specific absorption rate obtained when the imaging pulse sequence is executed on the object, and
wherein the SAR prediction unit, while causing the irradiation coil to irradiate the object with a high frequency magnetic field pulse in a state in which the object is disposed in the imaging space, detects a transmitted voltage and a reflected voltage of the irradiation coil, and then the SAR prediction unit determines a Q (quality) factor of the irradiation coil in the state in which the object is disposed in the imaging space and on the basis of the transmitted voltage and the reflected voltage, obtains a radio frequency (RF) absorption amount of the object on the basis of the Q factor, and predicts the SAR by using the RF absorption amount obtained based on the Q factor, and
the control section adjusts the imaging pulse sequence based on the predicted SAR received from the SAR prediction unit.

2. The magnetic resonance imaging apparatus according to claim 1, wherein the high frequency magnetic field pulse which is caused to be applied by the SAR prediction unit has a predetermined frequency, a standing wave ratio is obtained on the basis of the detected transmitted voltage and reflected voltage of the irradiation coil, and the Q factor is obtained by using the standing wave ratio.

3. The magnetic resonance imaging apparatus according to claim 2, wherein the SAR prediction unit obtains the Q factor corresponding to a value of the standing wave ratio on the basis of a relationship between a standing wave ratio and a Q factor, obtained in advance.

4. The magnetic resonance imaging apparatus according to claim 2, wherein a frequency of the high frequency magnetic field pulse is a resonance frequency of water.

5. The magnetic resonance imaging apparatus according to claim 1, wherein the SAR prediction unit causes the object to be irradiated with a high frequency magnetic field pulse having a predetermined frequency different from the high frequency magnetic field pulse for obtaining the Q factor, detects transmitted power and reflected power of the irradiation coil, and predicts the SAR by using a difference therebetween and the Q factor.

6. The magnetic resonance imaging apparatus according to claim 1, wherein the SAR prediction unit causes the high frequency magnetic field pulse to be applied for multiple times at different frequencies, detects a transmitted voltage and a reflected voltage of the irradiation coil for each irradiation, obtains impedances on the basis of the transmitted voltage and the reflected voltage, and obtains the Q factor by using a maximum value of the impedances.

7. The magnetic resonance imaging apparatus according to claim 6, wherein the SAR prediction unit obtains the Q factor by using a frequency at which the impedance becomes the maximum value, and frequencies at which the impedance becomes a half of the maximum value.

8. The magnetic resonance imaging apparatus according to claim 6, wherein the SAR prediction unit obtains the Q factor corresponding to the maximum value of the impedance on the basis of a relationship between a maximum value of the impedance and a Q factor, obtained in advance.

9. The magnetic resonance imaging apparatus according to claim 1, wherein the irradiation coil is connected to a signal line through which a high frequency signal for generating the high frequency magnetic field pulse is supplied, and the signal line is provided with a directional coupler which detects a transmitted voltage and a reflected voltage of the irradiation coil.

10. A magnetic resonance imaging apparatus comprising:
a static magnetic field generation section that applies a static magnetic field to an imaging space;
a bed on which an object is disposed in the imaging space;
a gradient magnetic field coil that applies a gradient magnetic field to the imaging space;
an irradiation coil that irradiates the imaging space with a high frequency magnetic field;
a reception coil that receives a nuclear magnetic resonance signal generated by the object in the imaging space; and
a control section that controls a timing at which the gradient magnetic field is applied from the gradient magnetic field coil and a timing at which the high frequency magnetic field is applied from the irradiation coil according to a predetermined imaging pulse sequence,
wherein the control section includes a specific absorption rate (SAR) prediction unit that predicts a specific absorption rate obtained when the imaging pulse sequence is executed on the object, and
wherein the SAR prediction unit causes the irradiation coil to irradiate the object with a high frequency magnetic field pulse in a state in which the object is disposed in the imaging space, detects a transmitted voltage and a reflected voltage of the irradiation coil, obtains a Q (quality) factor of the irradiation coil on the basis of the transmitted voltage and the reflected voltage, obtains a radio frequency (RF) absorption amount of the object on the basis of the Q factor, and predicts the SAR by using the RF absorption amount, and the control section adjusts the imaging pulse sequence based on the predicted SAR received from the SAR prediction unit, and
wherein the specific absorption rate (SAR) prediction unit obtains the RF absorption amount $P_{object}$ according to $P_{object}=(P_{fwd}-P_{rfl})*(1-Q/Q')$ where $P_{fwd}$ is transmitted power, $P_{rfl}$ is reflected power, Q is a Q factor value measured with the object in the irradiation coil, and Q' is a Q factor value measured without the object in the irradiation coil.

* * * * *